United States Patent [19]

Worsley

[11] Patent Number: 5,072,039

[45] Date of Patent: Dec. 10, 1991

[54] FEED SUPPLEMENT FOR RUMINANTS

[76] Inventor: Michael Worsley, 7624 - 132 Avenue, Edmonton, Alberta, Canada, T5C 2B1

[21] Appl. No.: 432,613

[22] Filed: Nov. 6, 1989

[51] Int. Cl.$^5$ .............................................. C07C 273/18
[52] U.S. Cl. ........................................ 564/60; 564/61
[58] Field of Search .................................... 564/60, 61

[56] References Cited

U.S. PATENT DOCUMENTS

| | | | |
|---|---|---|---|
| 2,315,745 | 4/1943 | Sorenson | 564/60 |
| 2,619,416 | 11/1952 | King | 564/60 |
| 2,673,859 | 3/1954 | Simons | 564/61 |
| 3,903,154 | 9/1975 | Singer | 564/60 |
| 4,203,892 | 5/1980 | Friedman | 530/345 |

OTHER PUBLICATIONS

Friedman, M., "Protective proteins for animal feed", CA: 93:112593, p. 580, 1980.

Marconi et al., "Removing petroleum contaminants from water", CA: 87:172675m, p. 297, 1977.

Primary Examiner—Richard L. Raymond
Assistant Examiner—Susan P. Trainer
Attorney, Agent, or Firm—E. Peter Johnson

[57] ABSTRACT

The invention includes a process wherein a solid, substantially non-polymerized aldehyde mono urea is produced if methanol or ethanol is used as the solvent for each of urea and an aldehyde in a reaction carried out under basic conditions. The process is useful in connection with making the following novel compounds: isobutyraldehyde mono urea, isovaleraldehyde mono urea, 2-methyl butyraldehyde mono urea and valeraldehyde mono urea. The compounds are useful as feed supplements for ruminants as they produce microbial attack-inducing acids and slowly release ammonia in the rumen.

2 Claims, 2 Drawing Sheets

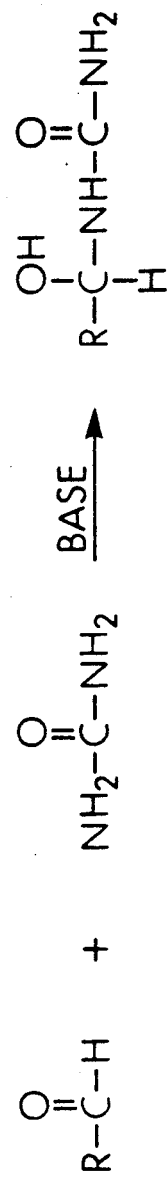

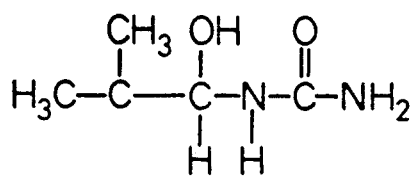
*Fig. 2a.* ISOBUTYRALDEHYDE MONO UREA
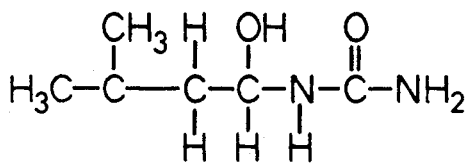
*Fig. 2b.* ISOVALERALDEHYDE MONO UREA
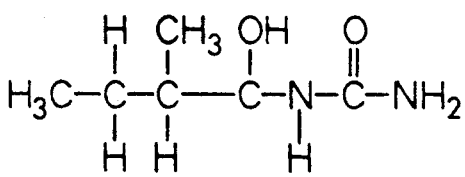
*Fig. 2c.* 2-METHYL BUTYRALDEHYDE MONO UREA
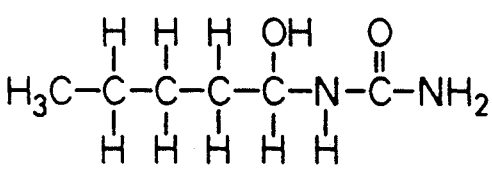
*Fig. 2d.* VALERALDEHYDE MONO UREA

FEED SUPPLEMENT FOR RUMINANTS

FIELD OF THE INVENTION

The invention relates to a group of novel compounds useful for feeding to ruminants and to a process for producing the compounds. The group of compounds consists of isobutyraldehyde mono urea, 2-methyl butyraldehyde mono urea, isovaleraldehyde mono urea, and valeraldehyde mono urea.

BACKGROUND OF THE INVENTION

Experimental work is on-going to improve the feed efficiency of ruminants. Two systems have gained ground in this regard.

One such system involves feeding a mixture of branched chain fatty acids to ruminants, to increase the microbial attack on the feed in the rumen. One commercial product of this type involved a mixture of isobutyric, isovaleric, valeric and 2 methyl butyric acids. The mixture was sold as a feed supplement for cattle under the trade mark Iso-acids by the Eastman Kodak Company.

The other system involves utilizing compounds as a feed supplement that are characterized by the slow release of ammonia, so that increased digestion is maintained over a prolonged duration. An example of this second system involves the feeding of glucose-urea compounds to ruminants.

It is desirable to provide compounds which, in the rumen, produce fatty acids and simultaneously and slowly release ammonia. Compounds having these dual capabilities have been developed. The compounds involved are branched chain aldehyde diureas.

The branched chain aldehyde diureas are produced by reacting alpha-methyl aldehydes with urea in water under acidic conditions. When the product of this reaction is introduced into the rumen and digested, the aldehyde is released and oxidized to yield a branched chain fatty acid. Simultaneously, the diurea hydrolyzes slowly to emit ammonia.

However, with respect to the fatty acids employed in the Iso-acid* mixture, only corresponding isobutyraldehyde and 2 methyl butyraldehyde are amenable to the aldehyde diurea process. Polymerization occurs if valeraldehyde or isovaleraldehyde are subjected to the process. In addition, the solubility characteristics in the rumen of the aldehyde diureas, produced by reacting isobutyraldehyde or 2 methyl butyraldehyde in accordance with the aldehyde diurea process, are relatively poor.

It is also known that formaldehyde and urea will react in water under basic conditions to form mono methylol urea. It was postulated by applicant that mono ureas could be produced from higher carbon aldehydes in the same manner; it was applicant's hope that such higher carbon mono ureas would be less polymerized and more soluble in water (and thus in the rumen) than the aldehyde diureas. However when experiments were carried out by applicant in accordance with:
reacting an aldehyde having 4 or 5 carbons with urea under basic condition
using water as the solvent
the reaction product was found to be a slime, because of the insolubility of the aldehydes

SUMMARY OF THE INVENTION

It has now been discovered that a solid, substantially non-polymerized aldehyde mono urea, which is easily handled and has partial solubility in water, is obtained if a solvent, selected from the group consisting of methanol and ethanol, is used for each of the urea and aldehyde in the reaction expressed by the following equation:

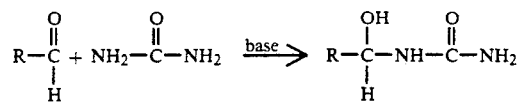

where R is a branched chain or linear alkyl group having 3 or 4 carbons.

DESCRIPTION OF THE DRAWINGS

FIG. 1 sets forth the reaction equation involved in the invention; and

FIG. 2 sets forth the aldehyde mono urea products of the invention.

DESCRIPTION OF THE PREFERRED EMBODIMENT

For laboratory synthesis, the following method was used:

Equimolar amounts of urea and aldehyde were added to the minimum amount of solvent alcohol required to form a solution at reflux temperature. With ethanol, the reflux temperature is about 75° C. More particularly, equimolar amounts of urea and aldehyde were added to ethanol in a ratio of 140 ml alcohol to 1 mole urea;

the aldehyde used was selected from the group consisting of isobutyraldehyde, isovaleraldehyde, 2-methyl butyraldehyde and valeraldehyde;

The mixture was made basic by addition of KOH to a pH of 10;

The mixture was then brought to reflux until a homogeneous solution resulted and reflux was continued thereafter for about 1 hour;

Vacuum was applied and part of the alcohol was distilled, leaving a solid;

The excess alcohol and aldehyde was removed from the solid by a stream of hot air;

After all the liquid was evaporated, the solid was washed well with water to remove excess urea;

The product solid was soluble in cold methanol. It should be noted that our reaction conditions are non-hydrogenating, since the temperature used is well below 100° C. and hydrogen is not introduced into the system. In order for hydrogenation to take place, temperatures greater than 100° C., high pressure, and introduction of hydrogen, ammonia and preferably a hydrogenation catalyst would be required. We do not use such hydrogenating conditions.

Isobutyraldehyde, isovaleraldehyde, 2-methyl butyraldehyde and valeraldehyde mono ureas were made using the above described procedure. Each of the compound products were analyzed for carbon, hydrogen, and nitrogen and subjected to nuclear magnetic resonance and infra red analysis. These analyses were consistent with the structures set forth in FIG. 1.

In an industrial version of the process (which omits washing), the solid product obtained typically contained 87% by wt. aldehyde mono urea and 13% unreacted urea. This version of the process involved using urea and aldehyde in equimolar amounts. The use of other ratios helped very little in the reaction. The alcohols were used at the minimum amounts to form a solution at the reflux temperature. KOH was added to adjust to a pH of ten. The solution was refluxed for one hour. The removal of the alcohol and unreacted aldehyde led to a product which was a solid and contained approximately 87% aldehyde mono urea and 13% unreacted urea, as aforesaid. This product can be fed to ruminants as is, since the urea is also digested.

The utility of isobutyraldehyde mono urea as a feed supplement for sheep was demonstrated by a feeding trial, as described below. Isovaleraldehyde, 2-methyl butyraldehyde and valeraldehyde mono ureas provide the same utility.

More particularly, a large batch of washed isobutyraldehyde mono urea ("IBMU") was made in accordance with the industrial version of the process except that the product was washed to remove urea as a factor in the trial. Fifteen sheep were used in a trial and divided into groups of three, each group being fed a diet of one of:
- hay alone (the control);
- hay plus soya meal as a supplement;
- hay plus canola meal as a supplement;
- hay plus urea as a supplement;
- hay plus 2% isobutyraldehyde mono urea as a supplement.

The test lasted for 60 days after allowing the sheep to adapt to the feed regime for 2 weeks.

The sheep each had a tube extending into the rumen and samples were taken therefrom with a syringe.

The release of ammonia in the rumen of the sheep was monitored over 8 hour periods, in accordance with the schedule shown in Table I. More particularly, analyses were carried out using an ammonium electrode. Table I shows typical effects of the supplements on the rumen ammonia concentrations (mg N/liter):

TABLE I

| Hours After Feeding | Control | Soya Meal | Urea | Canola | IBMU | SE | Sig § |
|---|---|---|---|---|---|---|---|
| 1 | 133.3c | 156.3b | 127.4c | 142.6c | 169.7a | 4.09 | 0.000 |
| 2 | 170.6c | 228.9b | 422.3a | 237.7b | 205.5b | 5.59 | 0.000 |
| 4 | 111.0c | 192.1b | 241.0a | 188.5b | 184.8b | 4.54 | 0.000 |
| 8 | 76.3c | 131.9b | 126.2b | 125.2b | 191.1a | 3.53 | 0.000 |

Standard error of the mean is based on 12 replications per mean.
§ Probability that difference is due to chance; a probability of 0.05 means that the same result would be achieved 5 times out of 100 by chance.
a-c Means not followed by the same letter differ significantly The data shows that ammonia is released from IBMU. Also, production of ammonia from IBMU in the rumen remains consistent through an 8 hour period. And the data supports the assertion that IBMU is a source of slow release ammonia.

In tandem with the ammonia production monitoring, the production of isobutyric acid in the rumen of the sheep was also monitored by analyzing the rumen samples by gas chromatograph. The results noted are set forth in Table II.

TABLE II

| Hours After Feeding | Diet | Acetic Acid | Propionic Acid | Isobutyric Acid | Butyric Acid | Isovaleric Acid | Valeric Acid |
|---|---|---|---|---|---|---|---|
| 0 | Control | 3.472 | 1.049 | .083a | .904a | .141a | .083ab |
|  | Soy | 3.658 | 1.078 | .092a | .869ab | .160b | .089a |
|  | Urea | 3.350 | 0.970 | .079a | .789c | .134a | .080b |
|  | Canola | 3.396 | 0.996 | .086a | .830bc | .154b | .083ab |
|  | IBMU | 3.531 | 1.062 | .158b | .918a | .141a | .091a |
|  | SE | 0.112 | 0.031 | 0.004 | 0.023 | 0.003 | 0.003 |
| 2 | Control | 4.007a | 1.399ac | .075a | 1.128a | .095ac | .107a |
|  | Soy | 4.296b | 1.486ab | .071a | 1.189ab | .114d | .116c |
|  | Urea | 3.932a | 1.359c | .062a | 1.010c | .089c | .095b |
|  | Canola | 4.392b | 1.516b | .076a | 1.274b | .123b | .131d |
|  | IBMU | 3.472a | 1.137d | .182b | .963c | .100a | .101b |
|  | SE | 0.087 | 0.036 | 0.005 | 0.031 | 0.003 | 0.003 |
| 4 | Control | 3.753ab | 1.313a | .055a | 1.095ab | .069a | .079a |
|  | Soy | 4.169b | 1.443a | .061a | 1.142a | .088b | .101b |
|  | Urea | 3.935b | 1.338a | .049a | .992bc | .061a | .078a |
|  | Canola | 4.002b | 1.393a | .063a | 1.133ab | .089b | .103b |
|  | IBMU | 3.458a | 1.116b | .200b | .923c | .073a | .078a |
|  | SE | 0.146 | 0.056 | 0.006 | 0.045 | 0.005 | 0.004 |
| 8 | Control | 3.811ac | 1.191ac | .058a | 1.114a | .080a | .072a |
|  | Soy | 4.209b | 1.331b | .061a | 1.131a | .095b | .087b |
|  | Urea | 3.893a | 1.219abc | .050a | .968b | .068c | .071a |
|  | Canola | 4.052ab | 1.312ab | .060a | 1.086a | .091b | .083b |
|  | IBMU | 3.609c | 1.114c | .219b | .960b | .081a | .076a |
|  | SE | 0.088 | 0.039 | 0.010 | 0.027 | 0.002 | 0.002 |

It can be seen from the data of Table II that the production of isobutyric acid from IBMU was greater than from the other supplements tested and that this production was increasing over the length of the test period while the production from the other sources was diminishing.

In summary, it was established that the aldehyde mono ureas of the invention are a good source of fatty acids and slow release ammonia in the rumen and therefore are useful as food supplements.

What is claimed is:

1. A process for producing solid alkyl aldehyde mono urea comprising:
reacting urea with an alkyl aldehyde, having the formula

wherein R is a branched chain or linear alkyl group having 3 or 4 carbons, under basic conditions and wherein each of the reactants is provided in a solvent selected from the group consisting of methanol and ethanol, under non-hydrogenating conditions.

2. The process as set forth in claim 1 wherein: the aldehyde is selected from the group consisting of isobutyraldehyde, isovaleraldehyde, 2-methyl butyraldehyde and valeraldehyde.

* * * * *